United States Patent [19]

Gay et al.

[11] Patent Number: 5,047,018

[45] Date of Patent: Sep. 10, 1991

[54] CATHETER AND STYLET ASSEMBLY HAVING DUAL POSITION STYLET

[75] Inventors: Eric L. Gay; Sheila J. Hanson; William G. O'Neill, all of St. Paul, Minn.

[73] Assignee: Minnesota Mining and Manufacturing Company, St. Paul, Minn.

[21] Appl. No.: 393,212

[22] Filed: Aug. 14, 1989

[51] Int. Cl.⁵ ............................................. A61M 5/178
[52] U.S. Cl. .................................... 604/164; 604/165; 128/657
[58] Field of Search ................... 604/95, 117, 164–166, 604/170, 280, 283; 128/657, 772

[56] References Cited

U.S. PATENT DOCUMENTS

| | | | |
|---|---|---|---|
| 1,060,665 | 5/1913 | Bell . | |
| 1,248,492 | 12/1917 | Hill | 604/165 |
| 2,393,003 | 1/1946 | Smith | 128/349 |
| 3,419,010 | 12/1968 | Williamson | 128/350 |
| 3,552,384 | 1/1971 | Pierie et al. | 128/657 |
| 3,757,768 | 9/1973 | Kline | 128/2 M |
| 3,854,473 | 12/1974 | Matsuo | 128/8 |
| 3,867,945 | 2/1975 | Long | 128/349 R |
| 3,923,066 | 12/1975 | Francisoud et al. | 128/348 |
| 4,137,916 | 2/1979 | Killman et al. | 128/214.4 |
| 4,273,131 | 6/1981 | Olsen | 128/341 |
| 4,504,268 | 3/1985 | Herlitze | 604/170 |
| 4,616,652 | 10/1986 | Simpson | 128/772 |
| 4,661,094 | 4/1987 | Simpson | 604/280 |
| 4,713,057 | 12/1987 | Huttner et al. | 604/164 |
| 4,834,709 | 5/1989 | Banning et al. | 604/170 |

FOREIGN PATENT DOCUMENTS 123520 8/1919 United Kingdom ................ 604/165

OTHER PUBLICATIONS

Sarns/3M Brochure, "Sterilized Disposable Instruments".
Flyer, "Vent Catheters", by Research Medical, Inc., Salt Lake City, Utah.
H. Zwart, J. Brainard and R. DeWall, "Ventricular Fibrillation Without Left Ventricle Venting", The Annals of Thoracis Surgery, 20: 418–423 (Oct. 1975).
C. Blanche, D. MacKay & M. Lee, "A New Overpressure Safety Valve for Use in the Venting Line During Cardiopulmonary Bypass", Mount Sinai Journal of Medicine, 53: 239–240 (Apr. 1986).

Primary Examiner—John D. Yasko
Assistant Examiner—Anthony M. Gutowski
Attorney, Agent, or Firm—Gary L. Griswold; Walter N. Kirn; Stephen W. Bauer

[57] ABSTRACT

A catheter and stylet assembly comprising an elongate catheter having a lumen open at the proximal and distal ends of the catheter, and a connector adjacent the proximal end of the catheter for connecting the catheter to an extracorporeal support system. A stiff-flexible stylet is provided that is slidably receivable in the lumen of the catheter for providing rigidity to the catheter to facilitate introduction of the catheter into a chamber of a heart or other organ. First and second shoulders are provided on the catheter for abutting a latching portion of the stylet to secure the stylet in either of two positions relative to the catheter. The two positions include a first position wherein the distal end of the stylet extends outwardly from the distal end of the catheter for introducing the catheter into an artery or vein, or directly through the heart wall, and a second position wherein the distal end of the stylet is received within the lumen of the catheter for positioning the catheter in the heart.

15 Claims, 1 Drawing Sheet

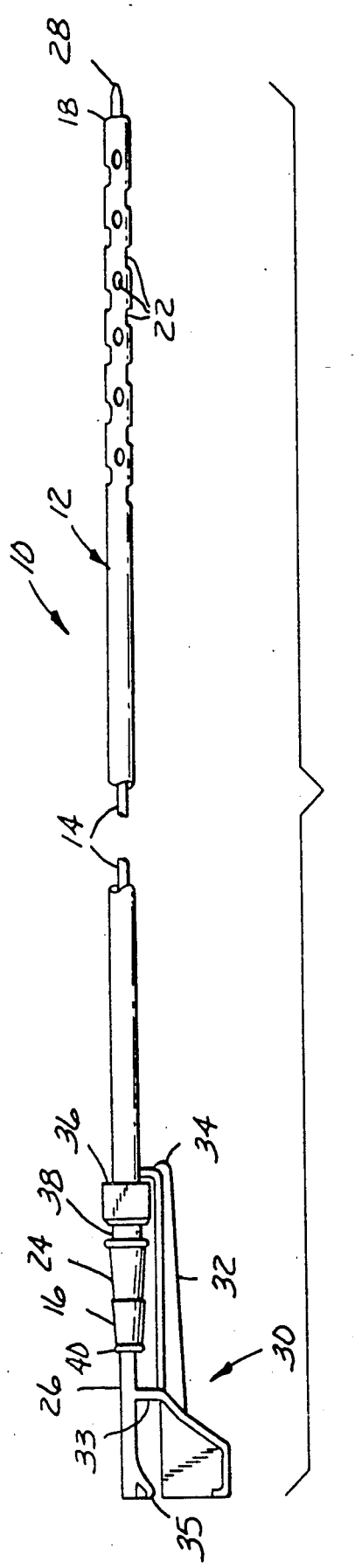
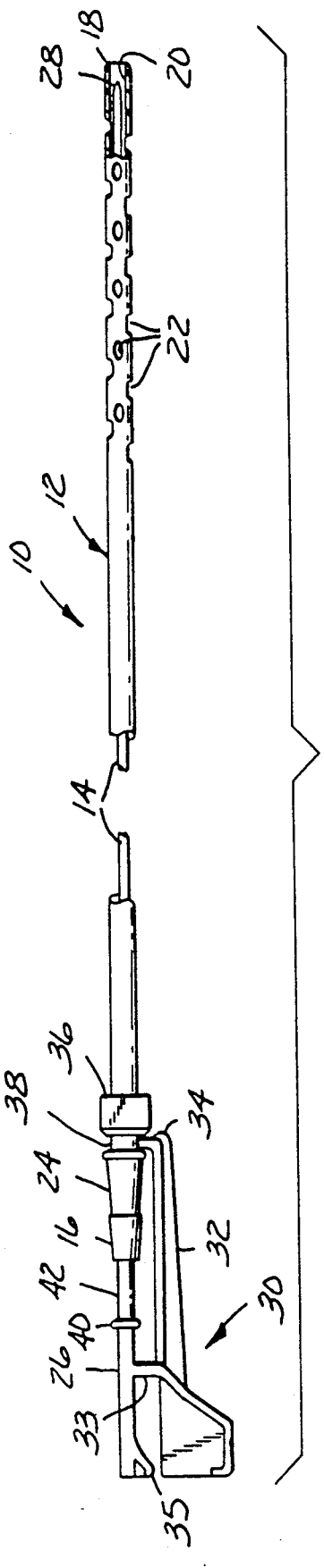

CATHETER AND STYLET ASSEMBLY HAVING DUAL POSITION STYLET

This invention relates to a catheter and stylet assembly useful for introducing a catheter into the heart or other organ of a patient.

BACKGROUND OF THE INVENTION

Surgeons typically "vent" or drain the left ventricle of the heart during cardiopulmonary bypass operations in order to reduce the pressure in the left ventricle, which otherwise may lead to overdistention (excessive stretching) of the left side of the heart and pulmonary veins. For example, the left ventricle may be vented with a catheter that is connected to an extracorporeal support system, including a pump for draining the chamber.

Vent catheters have conventionally been introduced into the left ventricle with the assistance of a relatively stiff stylet extending through the lumen of the catheter distally or outwardly beyond the distal end of the catheter. Such stylets provide sufficient rigidity to the catheter so that the catheter may be pushed through an incision into a pulmonary vein or directly through the wall of the heart, and the distal end of the stylet helps to stretch and open an opening through the vein or heart wall through which the catheter may be advanced. The catheter would then be positioned in the left ventricle with the distal end of the stylet extending outwardly beyond the distal end of the catheter.

One problem with such a procedure has been the risk of damaging heart tissue by scraping the tissue with the distal end or tip of the stylet, which is typically formed of relatively hard material, such as nylon. At least one surgeon has suggested performing cardiopulmonary bypass operations without venting the left ventricle to avoid this problem, notwithstanding the fact that left heart pressures are substantially higher without venting. See, for example, H. Zwart, J. Brainard, and R. DeWall, *Ventricular Fibrillation Without Left Ventricle Venting*, 20 The Annals of Thoracic Surgery 418–423 (October 1975).

One approach to this problem is shown in U.S. Pat. No. 4,834,709, which describes a soft silicone catheter having a closed rounded distal end that may be introduced into the left ventricle of the heart without the distal end of a stylet being exposed to heart tissue. Such a catheter protects heart tissue by effectively shielding the stylet within the relatively soft catheter. However as a result of closing the distal end of the catheter, the potential flow rate of fluid through the catheter is reduced relative to catheters that have open distal ends, and the stylet is rendered incapable of opening or stretching an opening through a vein or the heart wall.

Another approach has been to retract the stylet from its fully inserted position, where its distal end extends beyond the catheter, into the catheter so that the catheter houses or shields the distal end of the stylet. The catheter would then be inserted through an incision into a vein, artery or wall of the heart, without the distal end of the stylet stretching the incision. As a result, it is more difficult to insert the catheter through the vein, artery or heart wall than would be the case when the distal end of the stylet extends beyond the distal end of the catheter.

Relatively stiff vent catheters have also been used without stylets during cardiopulmonary bypass operations. Stiffness may be provided by embedding a malleable metal wire in the wall of the catheter. An urethral catheter having such an embedded metal wire is described in U.S. Pat. No. 3,867,945. Sarns, Inc., a subsidiary of Minnesota Mining and Manufacturing Company of St. Paul, Minn., has been selling a left heart vent catheter that has a preformed curved section generally adjacent the distal end of the catheter. This preformed catheter has sufficient rigidity for introduction into the heart without a stylet. However, soft, very flexible catheters are frequently desired for use in cardiopulmonary bypass operations, since the heart can be more readily manipulated and repositioned without interference from the catheter.

SUMMARY OF THE INVENTION

This invention provides a catheter and stylet assembly useful for introducing a vent catheter into the heart or other organ of a patient to drain accumulated fluid from the heart or other organ; that is designed to shield the distal end of the stylet inside the lumen of the catheter; and that is designed to reduce or eliminate the risk of damage to heart or other tissue due to contact with the distal end of the stylet. The stylet may be secured in either of two positions relative to the catheter, including a first position wherein the distal end of the stylet extends outwardly beyond the distal end of the catheter for introducing the catheter into an artery or vein, or directly through the heart wall, and a second position wherein the distal end of the stylet is fully received within the lumen of the catheter for positioning the catheter in the heart of a patient.

Generally, the catheter assembly of the invention comprises an elongate catheter having proximal and distal ends, and a lumen open at the proximal and distal ends of the catheter. Connecting means is provided adjacent the proximal end of the catheter adapted for connecting the catheter to an extracorporeal support system or the like. A stiff-flexible stylet is slidably receivable in the lumen of the catheter for providing rigidity to the catheter to facilitate introduction of the catheter into a chamber of a heart or other organ. The stylet has proximal and distal ends, and a length relative to the catheter sufficient to permit the distal end of the stylet to extend outwardly from the distal end of the catheter when the stylet is received in the catheter. Dual positioning means is provided generally adjacent the proximal ends of the stylet and catheter for releasably connecting the stylet to the catheter in the first and second positions.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein:

FIG. 1 is a side view of a catheter and stylet assembly of the invention, illustrating a first position of the stylet where the distal end of the stylet extends outwardly beyond the distal end of the catheter; and FIG. 2 is a side view similar to FIG. 1, illustrating a second position of the stylet where the distal end of the stylet is received within the lumen of the catheter.

DETAILED DESCRIPTION OF A PREFERRED EMBODIMENT

As shown in FIG. 1, a catheter and stylet assembly of the invention is designated in its entirety by the reference numeral 10. The catheter and stylet assembly 10 is especially designed for introducing a vent catheter 12 into the left ventricle of a heart for use during cardiopulmonary bypass in order to prevent overdistention of the left side of the heart and pulmonary veins. The assembly 10 is designed to reduce or eliminate the risk of damage to the heart during introduction of the catheter 12 into the left ventricle.

The catheter and stylet assembly 10 generally comprises the elongate vent catheter 12 and a deformable or preformable "stiff-flexible" stylet 14. As used herein "stiff-flexible" refers to the property of a stylet 14 that permits the stylet 14 to be bent or flexed, with the stylet 14 providing some resistance to the change in shape. Acceptable "stiff-flexible" stylets include conventional resilient, non-preformable plastic stylets, malleable wire stylets, and conventional plastic-coated metal wire stylets, although other types of "stiff-flexible" stylets may also be employed. The catheter 12 has proximal and distal ends 16 and 18, and a lumen 20 extending longitudinally through the catheter 12. The lumen 20 is open at the proximal and distal ends of the catheter 12, and the catheter 12 preferably has a plurality of openings 22 along the catheter 12 generally adjacent its distal end 18 communicating with the lumen 20 of the catheter 12. Connecting means, such as a generally frustoconical or tapered connector 24, is provided adjacent the proximal end 16 of the catheter 12 for connecting the catheter 12 to an extracorporeal support system or the like (not shown).

The catheter 12 is preferably formed of thin wall tubing, e.g., tubing having a wall thickness of approximately 1.2 mm. Suitable materials for the catheter 12 include an alloy of polyvinyl chloride (PVC) and polyurethane (PU), such as sold under the trade designation "Vythene" by Dexter Plastics Division of the Dexter Corporation, Pineville, N.C., although other materials, such as silicone or PVC, could also be employed.

The stylet 14 is slidably receivable in the lumen 20 of the catheter 12 to provide rigidity to the catheter 12 so that introduction of the catheter 12 into a chamber of a heart or other organ is facilitated. The stylet 14 has proximal and distal ends 26 and 28, and a length relative to the catheter 12 sufficient to permit the distal end 28 of the stylet 14 to extend outwardly from the distal end 18 of the catheter 12 when the stylet 14 is received in the catheter 12. The stylet 14 is preferably formed of a malleable metal wire (not shown), such as stainless steel or aluminum, having a generally hard biocompatible plastic coating, such as low density polyethylene, extruded over the wire. A plastic tip preferably formed of the same material as the plastic coating is mounted on an end of the wire by insert molding to form the distal tip or end 28, and a handle shown at 30 is mounted on the opposite end of the wire to form the proximal end 26 of the stylet 14.

Dual positioning means generally designated 30 is provided generally adjacent the proximal ends 16 and 26 of the stylet 14 and catheter 12. The dual positioning means 30 is designed for releasably connecting the stylet 14 to the catheter 12 in either of two positions: a first position shown in FIG. 1 wherein the distal end 28 of the stylet 14 extends outwardly from the distal end 18 of the catheter 12, and a second position shown in FIG. 2 wherein the distal end 28 of the stylet 14 is fully received in the lumen 20 of the catheter 12. The distal end 28 of the stylet 14 preferably extends outwardly beyond the distal end 18 of the catheter 12 by only a short distance (e.g., approximately 4 mm) in the first position, and the distal end 28 of the stylet 14 is retracted only a short distance inside the lumen 20 of the catheter 12 in the second position (e.g., approximately 10 mm from the distal end 18 of the catheter).

More specifically, the dual positioning means 30 preferably includes a cantilever arm 32 mounted on the stylet 14 adjacent the proximal end 26 of the stylet 14, with the arm 32 extending from adjacent the proximal end 26 of the stylet 14 generally toward the distal end 28 of the stylet 14 and terminating at a free end 34. The cantilever arm 32 has a latching portion 34 adjacent or along its free end 34, which is biased from an unlatched position (not shown) toward a latching position (FIGS. 1 and 2) for releasably securing the stylet 14 to the catheter 12 in the first and second positions. The cantilever arm 32 is in its unlatched position when it is moved radially outwardly relative to the longitudinal axis of the stylet 14, that is, when the latching portion 34 is moved generally downwardly in FIGS. 1 and 2 from the latching position shown in the drawing.

A short bridge member 33 connecting the arm 32 to the stylet 14 resiliently flexes in order to accommodate movement of the arm 32 between its latched and unlatched positions, while biasing the arm 32 toward its latched position. A stop 35 may be provided adjacent the proximal end of the handle 30 to limit flexure of the bridge member 33. The cantilever arm 32, bridge member 33, stop 35 and other components of the handle 30 are preferably integrally molded of acrylonitrile-butadiene-styrene (ABS) plastic.

First and second latch-receiving or abutment means are preferably provided along the catheter 12 for receiving the latching portion 34 of the arm 32 to secure the stylet 14 in the first and second positions, respectively. For example, the first latch-receiving or abutment means may comprise a circumferential shoulder 36 extending generally radially outwardly from the catheter 12 for preventing movement of the stylet 14 from the first position (FIG. 1) toward the second position (FIG. 2) when the latching portion 34 of the stylet 14 is abutting the shoulder 36, and the second latch-receiving or abutment means may include an annular groove 38 in the catheter 12 or connector 24 for receiving the latching portion 34 of the arm 32 to secure the stylet 14 in the second position (FIG. 2). In this example, the annular channel 38 is positioned along the catheter 12 between the proximal end 16 of the catheter 12 and the shoulder 36 of the catheter 12.

Various other configurations and designs of the first and second latch-receiving means are also contemplated, such as notches in or annular ridges along the catheter. The shoulder 36 may take the form of one of the walls forming an annular channel similar to channel 38, and the second latch-receiving or abutment means may take the form of a shoulder similar to shoulder 36. In any case, it will be observed that the first and second latch-receiving or abutment means provide one or more structures (e.g., shoulder 36 and channel 38) for abutting the latching portion 34 of the cantilever arm 32 to prevent movement of the catheter 12 distally relative to the stylet 14 from the first and second positions, respectively, when the latching portion 34 of the arm 32 is received in the first or second latch-receiving means.

The dual positioning means 30 preferably also includes an annular flange or ledge 40 extending generally radially outwardly from the stylet 14 adjacent the proximal end 26 of the stylet. The ledge 40 is adapted to engage the proximal end 16 of the catheter 12 when the stylet 14 is in the first position (FIG. 1) to prevent movement of the stylet 14 distally (rightwardly in the drawing) relative to the catheter 12 beyond the first position.

The outside diameter of the stylet 14 may be substantially smaller than the inside diameter of the catheter's lumen 20. In this case, a small portion 42 of the stylet 14 extending distally from the ledge 40 may have an increased diameter relative to the rest of the stylet 14 in order to be more closely received in the lumen 20 of the catheter 12. This increased diameter section 42 of the stylet preferably extends distally along the stylet 14 a distance (e.g., 32 mm) substantially as large as the distance (e.g., 44 mm) the cantilever arm 32 extends distally past the ledge 40. The portion 42 may also be reinforced to reduce bending of the stylet 14 adjacent the cantilever arm 32.

It may be observed from the foregoing that the dual positioning means 30 facilitates using the catheter and stylet assembly 10 in two different modes during surgery. The distal end 28 of the stylet 14 extends outwardly beyond the distal end 18 of the catheter 12 in the first mode or position (FIG. 1) to facilitate expanding an opening in a vein, artery, of the wall of the heart, through which the assembly 10 may be introduced into the left ventricle of the heart. After the distal end 18 of the catheter 12 is introduced into the left ventricle or other organ, the surgeon manually moves the stylet 12 from the first position (FIG. 1) to the second position (FIG. 2). Since the relatively hard stylet 14 is shielded or housed inside the relatively soft catheter 12 when in the second position, the heart tissue is protected from scraping or other damage that may otherwise be caused by an exposed distal end 28 of the stylet 14. When the stylet 14 is retracted to the second position (FIG. 2) with the latching portion 34 received in the annular groove 38, the surgeon can be confident that the distal end 28 of the stylet 14 is safely housed within the lumen 20 of the catheter 12.

As various changes could be made in the constructions described above without departing from the scope of the invention, it is intended that all matter contained in the description above or shown in the accompanying drawing be interpreted as illustrative and not in a limiting sense.

We claim:

1. A catheter assembly comprising:
   an elongate catheter having proximal and distal ends, and a lumen open at the proximal and distal ends of the catheter;
   connecting means adjacent the proximal end of the catheter adapted for connecting the catheter to an extracorporeal support system or the like;
   a stiff-flexible stylet slidably receivable in the lumen of the catheter for providing rigidity to the catheter to facilitate introduction of the catheter into a chamber of a heart or other organ, the stylet having proximal and distal ends, and a length relative to the catheter sufficient to permit the distal end of the stylet to extend outwardly from the distal end of the catheter when the stylet is received in the catheter; and
   dual positioning means generally adjacent the proximal ends of the stylet and catheter for releasably locking the stylet to the catheter in either of two positions, consisting of a first position wherein the distal end of the stylet extends outwardly from the distal end of the catheter, and a second position wherein the distal end of the stylet is received in the lumen of the catheter;
   the dual positioning means comprising a latching member mounted on the stylet adjacent the proximal end thereof, the latching member having a latching portion biased from an unlatched position toward a latching position for releasably securing the stylet in the first and second positions, and first and second latch-receiving means along the catheter for receiving the latching portion to secure the stylet in the first and second positions.

2. An assembly according to claim 1 wherein the catheter has a plurality of openings along the catheter adjacent the distal end thereof communicating with the lumen of the catheter.

3. A catheter assembly comprising:
   an elongate catheter having proximal and distal ends, and a lumen open at the proximal and distal ends of the catheter;
   connecting means adjacent the proximal end of the catheter adapted for connecting the catheter to an extracorporeal support system or the like;
   a stiff-flexible stylet slidably receivable in the lumen of the catheter for providing rigidity to the catheter to facilitate introduction of the catheter into a chamber of a heart or other organ, the stylet having proximal and distal ends, and a length relative to the catheter sufficient to permit the distal end of the stylet to extend outwardly from the distal end of the catheter when the stylet is received in the catheter; and
   dual positioning means generally adjacent the proximal ends of the stylet and catheter for releasably connecting the stylet to the catheter in two positions, including a first position wherein the distal end of the stylet extends outwardly from the distal end of the catheter, and a second position wherein the distal end of the stylet is received in the lumen of the catheter;
   the dual positioning means comprising a cantilever arm mounted on the stylet adjacent the proximal end thereof, the arm extending from adjacent the proximal end of the stylet generally toward the distal end of the stylet and terminating at a free end, the arm having a latching portion adjacent its free end biased from an unlatched position toward a latching position for releasably securing the stylet in the first and second positions, and first and second latch-receiving means along the catheter for receiving the latching portion of the arm to secure the stylet in the first and second positions, respectively.

4. An assembly according to claim 3 wherein the first and second latch-receiving means include first and second abutment means on the catheter for abutting the latching portion of the cantilever arm to prevent movement of the catheter distally relative to the stylet from the first and second positions, respectively, when the latching portion of the arm is received in the first or second latch-receiving means.

5. An assembly according to claim 4 wherein the first abutment means comprises a circumferential shoulder extending generally radially outwardly from the catheter for preventing movement of the stylet from the first position toward the second position when the stylet is abutting the shoulder, and the second abutment means comprising walls of the catheter defining an annular groove for receiving the latching portion of the arm to secure the stylet in the second position.

6. An assembly according to claim 5 wherein the dual positioning means further comprises a ledge extending generally radially outwardly from the stylet adjacent the proximal end thereof for engaging the proximal end of the catheter when the stylet is in the first position to prevent movement of the stylet distally relative to the catheter beyond the first position.

7. An assembly according to claim 6 wherein the annular channel is positioned along the catheter between the proximal end of the catheter and the shoulder of the catheter.

8. An assembly according to claim 3 wherein the second latch-receiving means is positioned along the catheter between the proximal end of the catheter and the first latch-receiving means.

9. A catheter assembly comprising:
an elongate catheter having proximal and distal ends, and a lumen open at the proximal and distal ends of the catheter;
a connector adjacent the proximal end of the catheter adapted for connecting the catheter to an extracorporeal support system or the like;
a stiff-flexible stylet slidably receivable in the lumen of the catheter for providing rigidity to the catheter to facilitate introduction of the catheter into a chamber of a heart or other organ, the stylet having proximal and distal ends, and a length relative to the catheter sufficient to permit the distal end of the stylet to extend outwardly from the distal end of the catheter when the stylet is received in the catheter;
the stylet having a latching portion generally adjacent the proximal end of the stylet, the latching portion being biased toward a latching position generally radially inward of an unlatched position relative to the longitudinal axis of the stylet; and first and second shoulders extending generally radially outwardly from the catheter generally adjacent the proximal end of the catheter for abutting the latching portion of the stylet when the latching portion is in its latching position to secure the stylet in either of two positions relative to the catheter, including a first position wherein the distal end of the stylet extends outwardly from the distal end of the catheter, and a second position wherein the distal end of the stylet is received within the lumen of the catheter.

10. An assembly according to claim 9 wherein the catheter has a plurality of openings along the catheter adjacent the distal end thereof communicating with the lumen of the catheter.

11. An assembly according to claim 9 wherein the stylet further comprises a cantilever arm extending from generally adjacent the proximal end of the stylet generally toward the distal end of the stylet and terminating at a free end, the arm having a portion adjacent its free end constituting the latching portion of the stylet.

12. An assembly according to claim 11 wherein the first shoulder is generally circumferential about the longitudinal axis of the catheter, the catheter including walls defining an annular groove between the walls and the second shoulder for receiving the latching portion of the cantilever arm to secure the stylet in the second position.

13. An assembly according to claim 12 wherein the stylet includes a ledge extending generally radially outwardly from the stylet adjacent the proximal end thereof for engaging the proximal end of the catheter when the stylet is in the first position, thereby to prevent movement of the stylet distally relative to the catheter beyond the first position.

14. An assembly according to claim 13 wherein the annular channel is positioned along the catheter between the proximal end of the catheter and the first shoulder of the catheter.

15. An assembly according to claim 11 wherein the second shoulder is positioned along the catheter between the proximal end of the catheter and the first shoulder of the catheter.

* * * * *